United States Patent [19]

Chang

[11] Patent Number: 4,970,154

[45] Date of Patent: Nov. 13, 1990

[54] METHOD FOR INSERTING FOREIGN GENES INTO CELLS USING PULSED RADIOFREQUENCY

[75] Inventor: Donald C. Chang, Houston, Tex.

[73] Assignee: Baylor College of Medicine, Houston, Tex.

[21] Appl. No.: 238,670

[22] Filed: Aug. 30, 1988

Related U.S. Application Data

[63] Continuation of Ser. No. 106,282, Oct. 9, 1987, Pat. No. 4,822,470.

[51] Int. Cl.$^5$ .............................................. C12N 13/00
[52] U.S. Cl. .................................. 435/172.2; 435/173; 935/52
[58] Field of Search .................. 435/172.1, 173, 172.2; 424/95; 128/804; 204/299 R; 935/52

[56] References Cited

U.S. PATENT DOCUMENTS

| | | | |
|---|---|---|---|
| 4,441,972 | 4/1984 | Pohl | 204/183.1 |
| 4,452,747 | 6/1984 | Gersonde et al. | 264/4.1 |
| 4,476,004 | 10/1984 | Pohl | 204/299 R |
| 4,524,079 | 6/1985 | Hofmann | 204/234 |
| 4,561,961 | 12/1985 | Hofmann | 204/299 R |
| 4,578,167 | 3/1986 | Schoner | 204/183.1 |
| 4,578,168 | 3/1986 | Hofmann | 204/299 R |
| 4,622,302 | 11/1986 | Sowers | 435/172.2 |
| 4,661,451 | 4/1987 | Hansen | 435/174 |
| 4,665,898 | 5/1987 | Costa et al. | 128/1.3 |
| 4,822,470 | 4/1989 | Chang | 204/299 R |
| 4,906,576 | 3/1990 | Marshall, III | 435/287 |

FOREIGN PATENT DOCUMENTS 8602377  4/1986  PCT Int'l Appl. .

OTHER PUBLICATIONS

Proceedings of International Symposium on Molecular Mechanisms of Membrane Fusion, Chang, D. C. and Hunt, J. R. p. 26 (1987).
Cell Fusion ed. by A. E. Sowers, "Electrofusion and Plant Somatic Hybridization", Bates, G. W., Nea, L. J., and Hasenkampf, C. A., Plenum Press, NY, pp. 479–496 (1987).
Cell Fusion by A. E. Sowers, "Microinjection of Culture Cells via Fusion with Loaded Erythrocytes", Schlegel, R. A. and Lieber, M. R., Plenum Press, NY, pp. 457–479, (1987).
Cell Fusion ed. A. E. Sowers, "Electrofusion Principles and Applications", Bates, G. W., Saunders, J. A. and Sowers, A. E., Plenum Press, NY, pp. 367–395, (1987).
J. Membrane Biol., Stinger, D. A. and Hui, S. W., 93:43–53 (1986).

(List continued on next page.)

Primary Examiner—John F. Niebling
Assistant Examiner—Isabelle Rodriguez
Attorney, Agent, or Firm—Fulbright & Jarowski

[57] ABSTRACT

Disclosed are an apparatus and a method for the poration and fusion of cells using high-power radiofrequency electrical pulses. The electrodes of the apparatus can be hand held or part of integrated equipment with special containers for cells. The electrodes, which are positioned equidistant from each other, are attached to a high power function generator. The power function generator can apply a continuous AC electrical field and/or a high-power pulsed radiofrequency electrical field across the electrodes. The alternating electrical field induces cell congregation by the process of dielectrophoresis. The high-power pulsed radiofrequency electrical field porates or fuses the cells. The method has the ability to porate or fuse biological cells with a very high efficiency. The method can be used to fuse or porate a variety of cells including animal cells, human cells, plant cells, protoplasts, erythrocyte ghosts, liposomes, vesicles, bacteria and yeasts. The method has the unique ability to porate or fuse cells in very small or very large numbers. During the poration or fusions, a variety of chemical agents including DNA, RNA, antibodies, proteins, drugs, molecular probes, hormones, growth factors, enzymes, organic chemicals and inorganic chemicals can be introduced into these cells. The method can also be used to produce new biological species, to make hybridoma cells which produce animal or human monoclonal antibodies and to insert therapeutic genes into human cells which can be transplanted back into the human body to cure genetic diseases.

9 Claims, 12 Drawing Sheets

OTHER PUBLICATIONS

J. Cell Biology, Sowers, A. E., 103:1358–1362 (1986).
Exp. Cell Res., Kubiac, J. Z. and Tarkowski, A. K., 157:561–566 (1985).
Nature, Lo et al., 310:794–796 (1984).
Arch. Microbiol., Halfmann, H. J., Emeis, C. C. and Zimmerman, U., 134:1–4 (1983).
J. Membrane Biol., Holzapfel, C., Vienken, J. and Zimmerman, U., 67:13–26 (1982).
Science, Teissie, J., Knutson, V. P., Tsong, T. Y. and Lane, M. D., 216:537–538 (1982).
J. Membrane Biology, Zimmerman U., and Vienken, J., 67:165–182 (1982).
J. Cell Biology, White, J., Matlin, K. and Helenius, A., 89:674–679 (1981).
Biochimica et Biophysica Acta, Zimmerman, U. and Scheurich, P., 641:160–165 (1981).
J. Biol. Phys., Pohl, H. A., Kaler, K. and Pollock, K., 9:67–86 (1981).
Bioelectrochemistry and Bioenergenics, 7:553–574 (1980) or J. Electroanal. Chem., 116:553–574 (1980).
Naturwissenschaften, Neuman, E., Gerisch, G. and Opatz, K., 67:414–415 (1980).
Nature, Galfre, G. et al., 266:550–552 (1977).
Somatic Cell Genetics, Davidson, R. L., O'Malley, K. A. and Wheeler, T. B., 2:271–280 (1976).
J. Electrochem Society, Schwan, H. P. and Sher, L. D., 116:22C–26C (1969).
Current Protocols in Molecular Biology in "Introductions of DNA into Mammalian Cells", eds. Ausubel, F. M., et al., John Wiley & Sons New York, pp. 9.0.1–9.9.6 (1968).
Int'l. J. of Quantum Chemistry and Quantum Biology, Pohl, H. A. 9:399–409 (1982).
Chemical Abstract, 97:210964w R.375 (1982).

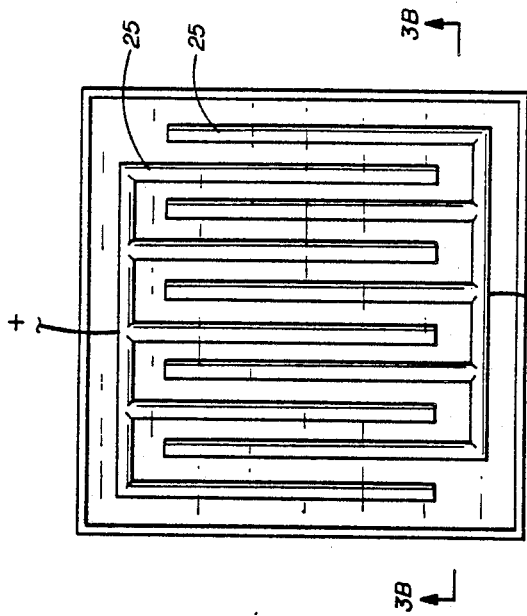
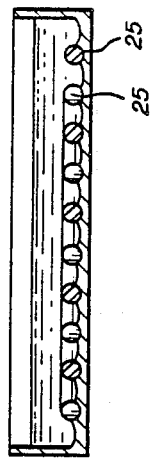
FIG. 3A
FIG. 3B
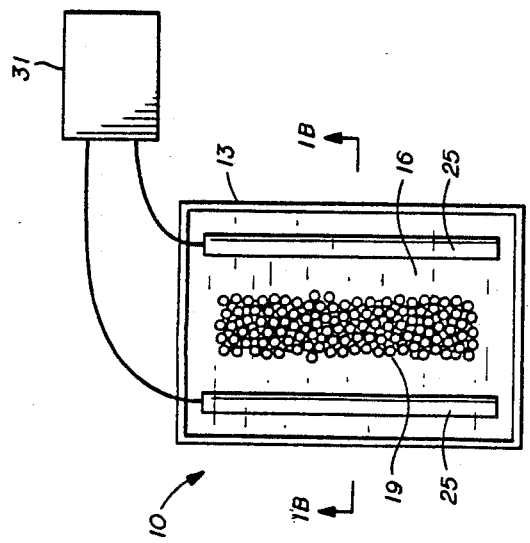
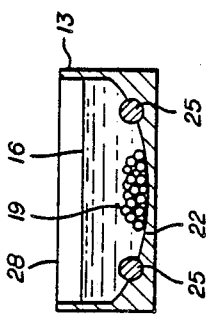
FIG. 1A
FIG. 1B

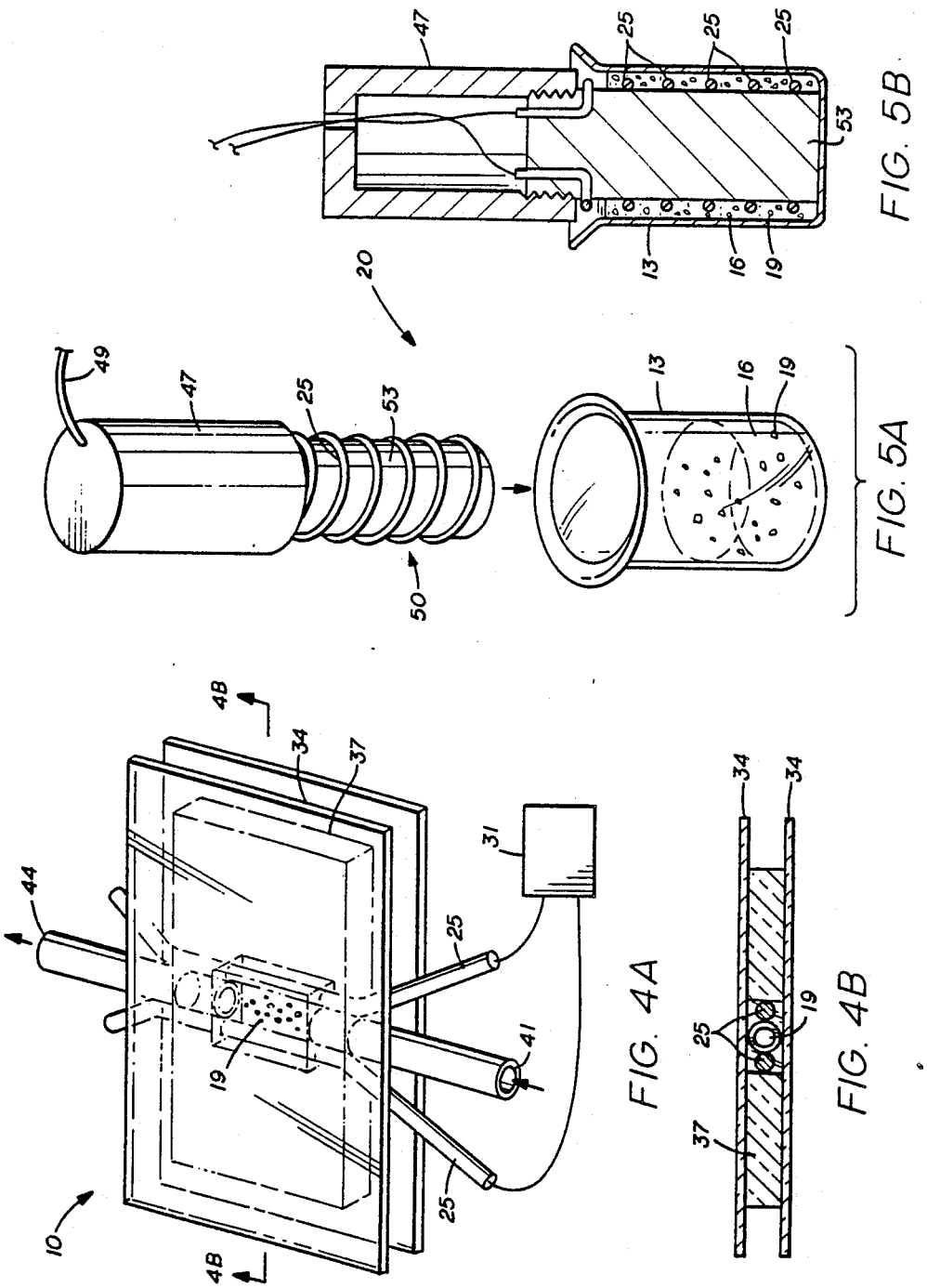

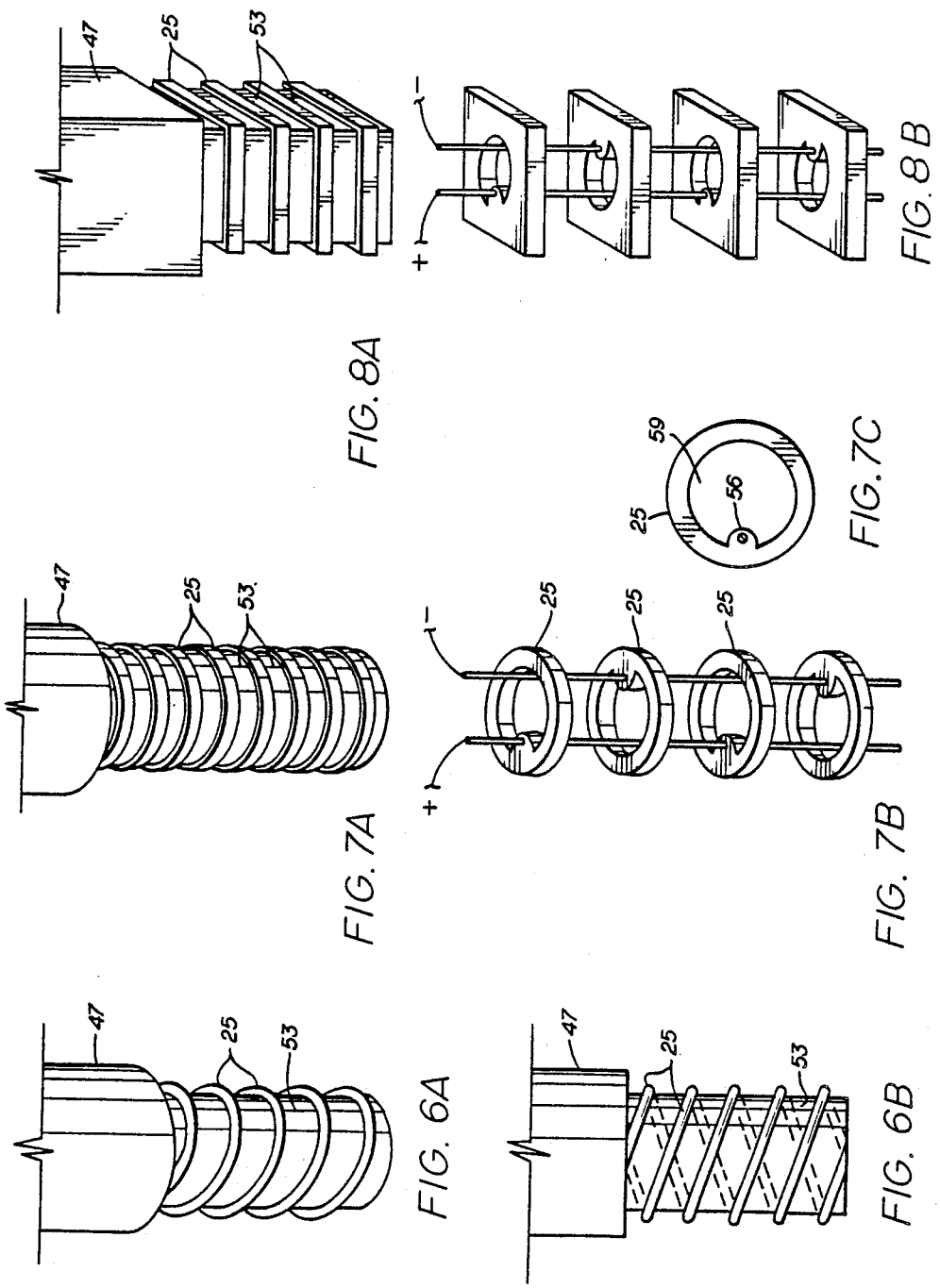

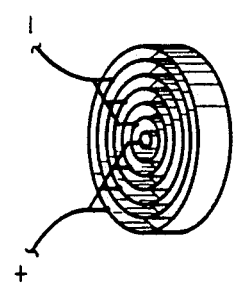
FIG. 11A
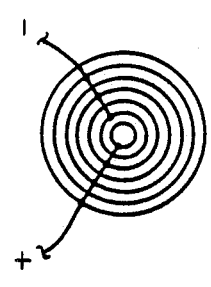
FIG. 11B
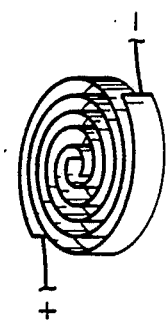
FIG. 10A
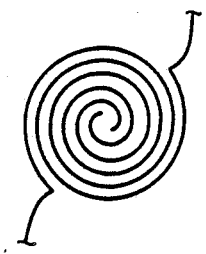
FIG. 10B
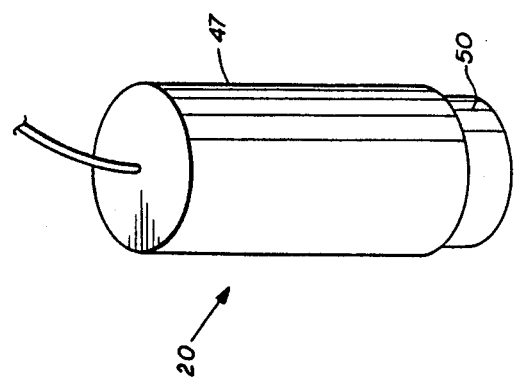
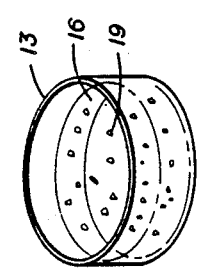
FIG. 9

METHOD FOR INSERTING FOREIGN GENES INTO CELLS USING PULSED RADIOFREQUENCY

CROSS REFERENCE TO RELATED APPLICATION

This Application is a continuation-in-part of Applicant's co-pending Application Ser. No. 106,282 filed Oct. 9, 1987, now U.S. Pat. No. 4,822,470.

FIELD OF THE INVENTION

This invention relates to the field of poration and fusion of biological cells by application of a high-power pulsed radiofrequency electric field. More particularly, it relates to permeabilizing and fusing cells in a wide variety of fields including gene transfection, microinjection of cells, production of monoclonal antibodies and making new biological species by hybridization.

BACKGROUND

Cell poration and cell fusion play a very important role in modern biotechnology. For example, one key procedure in genetic engineering is the introduction of exogeneous genetic material into a host cell. This insertion of genes is accomplished by either permeabilizing the cell membrane to allow entry of genetic material (i.e., gene transfection) or fusing the host cell with a cell containing the desired genetic material. Cell fusion is also important in the production of monoclonal antibodies. The process of producing monoclonal antibodies requires the fusion of antibody producing cells with continuously dividing cancer cells. (Galfre, G. et al., Nature 266:550-552 (1977); Lo, M. M. S. et al., Nature 310:794-796 (1984)). Additionally, one highly effective method of delivering drugs which normally cannot enter a cell is to fuse the cell with liposomes or red blood cell ghosts that have been pre-loaded with specific drugs. (Schlegel & Lieber, *Cell Fusion*, ed. by A. E. Sowers, Plenum Press (1987)).

The conventional techniques of cell fusion rely mainly on the actions of viruses (White, J. et al., J. Cell Biol. 89:674-679 (1981)); or chemical agents such as polyethylene glycol (Davidson, R. L. et al., Somatic Cell Genetics 2:271-280 (1976)). Virus-induced and chemical-induced fusion methods have many shortcomings. Not only is the fusion yield often very poor, typically less than 0.01%, but the standard fusion techniques may also cause severe side effects on the fused cells, thus greatly limiting their usefulness for many systems.

Alternative methods which induce cell fusion and cell poration by electric fields have been developed. (Pohl, U.S. Pat. No. 4,476,004; Sowers, U.S. Pat. No. 4,622,302; Schoner, U.S. Pat. No. 4,578,167; Neumann, E. et al. Naturwissenschaften 67:414-415 (1980); Zimmerman, U. and Nienken, J., J. Membrane Biol. 67:165-182 (1982); Bates G. W., et al., *Cell Fusion*, Plenum Press pp. 367-395 (1987)). The basic principle of these methods of electrofusion is to apply a pulsed high strength direct-current (DC) electric field across the cell. This DC field is usually generated by briefly switching on a DC power source or by discharging a capacitor. The applied DC field has a strength of several kilovolts per centimeter. This external electric field induces a large cell membrane potential. When the membrane Potential is of sufficient magnitude, a reversible breakdown of a small area of the cell membrane occurs. The breakdown results in the formation of physical pores at the surface of the cell. This process is called electroporation. Intracellular and extracellular material can exchange through the pore while it is open. After the DC field is removed, the pore will normally reseal quickly. When a pore is created between two closely adjacent cells a cytoplasmic bridge is formed via the pore. When the DC field is turned off the pore cannot reseal. Instead, the cytoplasmic bridge usually begins to enlarge, eventually causing the two cells to fuse.

Although the DC electrofusion method has been used successfully for a number of biological cells, including plant protoplasts (Zimmerman, U. et al., Biochem. Biophys. ACTA 641:160-165 (1981); Bates, G. W. et al., *Cell Fusion*, Plenum Press pp. 479-496 (1987)); blood erythrocytes (Sowers, A. E., J. Cell. Biol. 102:1358-1362 (1986); Chang and Hunt, *Proceedings of the International Symposium on Molecular Mechanisms of Membrane Fusion*, Buffalo, N.Y. pp. 26 (1987); Stenger, D. A. and Hui, S. W., J. Membrane Biol. 93:43-53 (1986)); tumor cells (Lo, M. M. S. et al., Nature 310:794-796 (1984); Tessie, J. et al., Science 216:537-538 (1982)); yeast cells (Halfmann, H. J., et al., Archiv. Microbiol. 134:1-4 (1983)); and blastomerers and eggs (Kubiac, J. Z. and Jarkowski, A. K., Exp. Cell Res. 157:561-566 (1985)), there are still many limitations to the use of this method. First, not all cell types can be fused with the same ease. In fact many cell types are extremely difficult to fuse with DC pulses. Second, there are many unknown factors which influence fusion yield. Fusion of certain cell types may be successful in one laboratory but not in others. The DC pulse method is still more of an art than a well understood procedure. Third, it is very difficult to use the DC pulse method to fuse cells of different sizes. This later problem occurs because the membrane potential induced by the external DC field is proportional to the diameter of the cell. Thus, the induced potential is larger for bigger cells. It is nearly impossible to chose a proper field strength of external field in order to fuse cells of two different sizes. When the external field is just sufficient to cause membrane breakdown in the larger cell, it is inadequate to induce a critical membrane potential in the smaller cell. On the other hand, if the external field is elevated to cause a membrane breakdown in the small cell, the large potential induced in the larger cell will cause an irreversible membrane breakdown and destroy the cell.

The present invention provides an improved method of cell poration and cell fusion which overcomes the above problems. Unlike the conventional electrofusion method which employs DC Pulses to induce membrane breakdown, the present invention uses a pulse or pulse of radiofrequency (RF) electric field to reversibly permeabilize cells and induce cell fusion. The high-power RF field produces an oscillating motion of the cell membrane through a process of electro-compression. Permeabilization of the cell membrane is caused by a combination of electrical breakdown and a localized sonication induced from the RF field. Thus, this oscillating electric field is more effective in breaking down the cell membrane than a DC field. Since this new method uses only physical means (i.e., RF electrical energy) to induce cell poration and cell fusion, it is free of biological or chemical contamination. The present invention produces results in seconds, provides much higher yields than conventional methods, and has minimal biological side effects. Thus, it is a clean, fast, efficient and safe method.

The improved efficiency of cell poration and cell fusion offered by the method of this invention has a particular significance in medical applications. One example is to produce antibodies for therapeutic uses. Since the human body usually rejects animal antibodies, such therapeutic antibodies must be produced by hybridomas of human cells; however, human hybridomas are extremely difficult to form by conventional methods (including electro-fusion by DC field). The method of the present invention will help to improve the efficiency in forming human hybridomas. Another example of medical application of this method is gene therapy. Many genetic diseases can be treated by inserting a therapeutic gene into the patient's cells in vitro and then transplanting the cells back to the patient's body. The conventional methods of cell poration (including the DC field method) usually require a large number of cells (typically 5-10 million cells) to perform a gene transfection and, as a result, are unsuitable for use in human therapy. In contrast, the method of the present invention has been demonstrated to be able to transfect cells in small numbers with high efficiency, and will be highly useful for gene therapy.

SUMMARY OF THE INVENTION

An object of the present invention is a method for the poration of cells.

An additional object of the present invention is a method for the fusion of cells.

A further object of the present invention is a device for the poration and fusion of cells.

Another object of the present invention is a method for inserting genetic materials into biological cells.

A further object of the present invention is the treatment of genetic disease by inserting therapeutic genes into cells that are transplanted into diseased patients.

Another object of the present invention is a method for the formation of hybridoma cells by the fusion of cells with RF electric field.

An additional object of the present invention is a method which greatly enhances the efficiency of producing monoclonal antibodies.

Another object of the present invention is the formation of a new species by the fusion of cells from different species using high-power RF pulses.

An additional object of the present invention is the introduction of chemicals and biological molecules into cells by the procedures of poration and/or fusion.

Thus, in accomplishing the foregoing objects there is provided in accordance with one aspect of the present invention a method for poration of biological particles comprising the steps of placing a plurality of biological particles in solution between two electrodes and applying a high-power pulsed RF oscillating field across the electrodes for porating the particles. The biological particles can either be suspended cells in solution or attached cells in cell culture. An additional embodiment of this method includes fusing the biological particles by placing the suspended biological particles in a container which allows the biological particles to congregate before applying the pulsed RF field.

An alternative method includes fusing the biological particles by applying a low power (e.g., 100 to 400 V/cm) alternating current (AC) electrical field before and/or after the pulsed RF oscillating field. The low-power electric field can cause the particles to move dielectrophoretically to form "pearl chains".

The biological particles can be a variety of materials including biological cells (human, animal or plant cells), liposomes, vesicles, erythrocyte ghosts, protoplasts, bacteria, and yeasts.

The pulsed RF field applied for the poration and fusion of cells can be an oscillating field of a single frequency or a mixed frequency. The RF oscillating field may be in the frequency range of 10 KHz to 100 MHz with a pulse width of about 1 $\mu$sec to 10 msec and a pulse amplitude of up to about 20 KV/cm. In a preferred embodiment the RF oscillating field is about 0.02 to 10 MHz and the pulse width is about 20 to 2000 $\mu$sec and the pulse amplitude is about 2-10 KV/cm. The wave form of the RF field may be sinusoidal, triangular, sawtooth, or square waves.

Another aspect of the present invention is the fusion of cells for the formation of new species, the introducing of chemical agents and natural or man-made genetic material into cells, and the formation of hybridoma cells. By the appropriate selection of cell types and materials new species can be formed either by the combining of genetic material from two different species by the fusion of their cells, or by the isolation or synthesis of the genetic material, and then the introduction of the genetic material into cells by either poration or fusion. Hybridoma cells are made by the fusion of antibody producing cells with continuously dividing cancer cells. Chemicals, drugs, DNA, RNA and other molecules can be introduced into cells by preloading vesicles, liposomes or erythrocyte ghosts before fusion with target cells.

Another aspect of the present invention is a device for the poration or fusion of biological particles comprising a container of non-conducting material capable of holding liquid and including an access port for receiving the biological particles. The device also includes electrodes positioned equidistant from each other and inserted into the container. A high-power function generator is attached to the electrodes and is capable of generating a RF electric field and/or an alternating electric field. In one embodiment the container is shaped to allow the biological particles to congregate.

An additional aspect is a device for poration and fusion of biological particles comprising a glass chamber and used with an optical microscope for observation of the poration and fusion of cells.

A further aspect is a cell poration and fusion device which can be hand-held. This device includes a handle and equidistant electrodes. The electrodes can be side-attached or bottom-attached and can be designed in a variety of shapes including rings, circles, double helices, squares, ellipses, concentric rings, concentric squares, interdigitating arrays, spirals and parallel plates.

Other and further objects, features and advantages will be apparent from the following description of the presently preferred embodiment of the invention given for the purpose of disclosure when taken in conjunction with the accompanying drawings.

BRIEF DESCRIPTION OF THE DRAWINGS

The invention will be more readily understood from a reading of the following specification by reference to accompanying drawings, forming a part thereof, where examples of embodiments of the invention are shown and wherein:

FIG. 1 is a schematic of one form of the present invention using a chamber which allows for the congregation of cells by gravity. 1A is a top view of the device and 1B is a cross-sectional view of the device showing the fusion chamber.

FIG. 3 is a schematic of one form of the present invention showing a large volume chamber for cell poration and/or cell fusion. 3A is a top view of the fusion chamber and 3B is a cross-sectional view showing the arrangement of electrodes in the chamber.

FIG. 4 is a schematic of a chamber for cell poration and/or cell fusion for optical microscopic observation. 4A is a elevational view of the chamber and 4B is a cross-sectional view of the chamber.

FIG. 5 is a schematic of a hand-held device for cell poration and/or cell fusion using a side contact configuration. 5A shows an elevational view of the device and 5B shows a cross-sectional view of the electrode inserted inside the cell container.

FIG. 6 is a schematic of a double helical design for the side-contact electrode assembly. 6A shows a elevational view of the helical design for the electrode assembly and 6B shows a side view of the same assembly.

FIG. 7 is a schematic view of a segmented ring design for the side-contact electrode assembly. 7A shows an elevational view of the electrode assembly, 7B shows the connection of the electrode rings in the electrode assembly and 7C is a top view of a single electrode ring.

FIG. 8 is schematic of a rectangular electrode assembly for cell poration and cell fusion. 8A shows an elevational view of the electrode assembly and 8B shows the connection of the electrode squares in the electrode assembly.

FIG. 9 is a schematic of a cell fusion and cell poration device with a bottom-contact configuration of electrodes.

FIG. 10 is a schematic of the double spiral design for the bottom-contact electrode assembly. 10A shows a elevational view and 10B shows top view of the electrode.

FIG. 11 is a schematic view of a concentric ring design for the bottom-contact electrode assembly. 11A shows an elevational view and 11B shows a top view of the electrode.

DETAILED DESCRIPTION

Figure 2A:
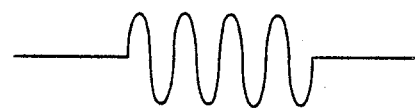
FIG. 2 is a graph of examples of the radiofrequency (RF) pulses used in the present invention. 2A is a single-frequency symmetrical RF pulse, 2B is an asymmetrical RF pulse, 2C is a multiple-frequency RF pulse, 2D is consecutive RF pulses of different frequencies and 2E is a low-power AC field followed by a high-Power RF pulse followed by a low-power AC field.

In the descriPtion which follows, like parts are marked throughout the specifications and drawings with the same referenced numerals. The drawings are not necessarily to scale and certain features of the invention may be exaggerated in scale or shown in schematic form in the interest of clarity and conciseness. It will be readily apparent to one skilled in the art that various substitutions and modifications may be made to the invention disclosed herein without departing from the scope and spirit of the invention.

One embodiment comprises a method for poration of biological particles comprising the steps of placing the biological particles in solution between two electrodes and applying a pulsed radiofrequency (RF) oscillating electric field across the electrodes, FIG. 1. A variety of biological particles can be used including biological cells, erythroycte ghosts, liposomes, protoplasts, bacteria and yeasts. The biological particles can be suspended cells in solution or can be attached cells in cell culture.

When a cell is placed in an electric field, an electrical potential is induced across the cell membrane. For a spherical cell, the membrane potential induced by an external electric field is $$V_m = 1.5 \, rE \cos \theta \tag{1}$$

where r is the radius of the cell, E is the strength of the external field and θ is the angle between the direction of the external field and the normal vector of the membrane at the specific site.

The induced electric field within the membrane is $$E_m = V_m/d = 1.5 \, (r/d) \, E \cos \theta \tag{2}$$

whee d is the thickness of the membrane. Since d is much smaller than r (d is about $6 \times 10^{-7}$ cm while r is in the order of several microns $E_m$ is about 1000 fold larger than the applied field, E. The large electric field within the membrane produces two effects. First, it exerts a strong force on the phosphate head group of the lipid molecules in the membrane and tends to move them in the direction of the field. Secondly, it compresses the membrane. When the external electric field oscillates, the lipid molecules within the membrane also undergo an oscillating motion.

In this arrangement, the cell itself functions as an antenna and the membrane is a transducer which converts the electrical oscillation into a mechanical oscillation. Thus, it is possible to generate an ultrasonic motion in the cell membrane by applying an external RF field. Because the induced potential at a given site of the membrane is a function of the angle between the orientation of the membrane and the electric field vector, the induced potential is not uniform over the entire cell surface. The applied energy is focused at the poles of the cell, that is, at $\theta = 0°$ or $180°$. Because the amplitude of the external field can be adjusted such that there is sufficient sonication power to break down the cell membrane at the poles but not at other parts of the membrane, the sonication can be localized. Experiments indicated that this localized membrane breakdown induced by the externally applied pulsed RF field is reversible. That is, the pore(s) induced by the RF field reseal quickly (within minutes) after the field is turned off. Furthermore, most of the cells apparently stay viable.

Such temporary permeabilization of the cell membrane is called cell poration. During this time period when pores are formed, a brief exchange of intracellular and extracellular materials occur. Many molecules, including drugs, antibodies, and gene segments, which normally cannot penetrate the cell membrane, can enter the cell through the temporarily opened pores that were induced by the pulsed RF field.

Another embodiment of this invention comprises a method for fusing cells. In order for biological particles to be fused, they must be in close proximity. When cells are in close proximity they are said to congregate. Two alternative procedures may be used to congregate the cells before fusion. In one, a container with a shape that allows the biological particles to congregate by gravity is used. For example, the bottom of the container can be made in a concave shape (see FIGS. 1 and 3). This allows the cells to congregate. When the cell membranes are permeabilized by the applied RF field, the closely adjacent cells can form cytoplasmic bridges. This process results in the fusion of cells.

Alternatively, a low amplitude continuous alternating current (AC) electrical field can be applied across the two electrodes. The frequency ranges from about 60 Hz to about 10 mega Hz. Typically a 100-400 V/cm field strength is used. Under the low amplitude AC field the cells act as dipoles and line up parallel to the field, eventually forming a long chain of cells which appear like "pearl chains". This process is called "dielectrophoresis" (Schwan, H. P. and Sher, L. D., J. Electrochem. Soc. 116:22C-26C (1969); Pohl, H. A. et al., J. Biol. Phys. 9:67-86 (1981)). Formation of this pearl chain normally takes about a few seconds to one minute.

The present invention uses a pulsed RF field to porate and/or fuse cells and has a clear advantage over the conventional electro-fusion method that uses a pulsed DC field. First, the RF field is a much more efficient means of transmitting energy to the cell membrane than the direct current field. The present invention utilizes a localized sonication to break down the cell membrane. This method is much more effective than the DC pulse method which relies solely on the electrical breakdown. The cell membrane is composed of macromolecules which have characteristic frequencies of thermal motion. When the frequency of the applied oscillating field matches one of these natural frequencies, a condition of resonance is reached, and the efficiency of energy transfer is greatly enhanced. In real biological cells the resonance peak can be very broad. The pulsed radiofrequency field can be carefully varied to achieve the proper resonant frequency for the cells of interest. Consequently, the ability to induce membrane breakdown will require less power than using a direct current field and results in less risk of irreversibly damaging the cell.

Second, this invention overcomes the difficulties encountered when the conventional methods are used to fuse cells of different size. In order to produce an electrical breakdown of the cell membrane, the field-induced membrane potential must exceed a certain critical value, $V_c$ (typically 1 volt). Such breakdown can be reversible, and the membrane will reseal after the external field is turned off if the induced membrane potential is not too much larger than $V_c$. The cell normally remains viable after such reversible breakdown. On the other hand, if the induced potential is much higher than $V_c$, the membrane breakdown is irreversible, the cell is permanently damaged, and will not remain viable.

From Eq. 1 it can be seen that when cells of different sizes are placed inside an electric field, the induced membrane potential is higher for the larger cell than for the smaller cell. This size-dependence of membrane potential causes a problem when attempting to fuse cells of different sizes using a DC field. Assume that two cells, A and B, are to be fused and that the radius of cell A, $r_a$, is about twice as big as the radius of cell B, $r_b$. In order to cause a reversible membrane breakdown in cell B, the applied external field must be sufficient so that 1.5 E $r_b$ is greater than $V_c$. However, the same applied electric field will induce a much larger $V_m$ in Cell A, and will cause an irreversible breakdown of the membrane leading to damage to this cell. Thus it is very difficult to use direct current pulses to fuse cells of significantly different sizes.

This problem can be solved by applying a pulsed radiofrequency field. When the applied field is a radiofrequency oscillating field instead of a DC field, the amplitude of the induced membrane potential is a function of the frequency. The membrane potential predicted in Eq. (1) is derived under the steady state condition. The induced potential does not arise instantaneously upon the application of the external field. If the external field is stationary, the membrane potential will reach $V_m$ given a sufficient time. The time required to establish this steady state membrane potential is called "relaxation time", or $\tau$, which is given by $$1/\tau = 1/R_m C_m + 1/r C_m (R_i + 0.5 R_e) \tag{3}$$

where $R_m$ and $C_m$ are specific resistance and specific capacitance of the membrane, and $R_i$ and $R_e$ are the specific resistances of the intracellular medium and the extracellular medium, respectively. (C. Holzapfel et al., *J. Membrane Biol.*, 67:13–26 (1982)). For a cell of several microns in diameter, $\tau$ is typically in the order of 1 μsec.

Since $R_m$ in most cells is very large, for practical purposes, eq. (3) can be simplified to $$\tau = rC_m(R_i + 0.5R_e) \quad (4)$$

Thus the relaxation time is approximately proportional to the radius of the cell.

Because the build-up of the membrane potential requires a time period characterized by the relaxation time $\tau$, the membrane potential induced by a RF field is frequency dependent. If a radiofrequency field is applied at a frequency smaller than $1/\tau$, the membrane potential has no problem in following the external field. The applied field will produce a 100% cellular response in $V_m$. On the other hand, if the frequency of the applied radiofrequency field is greater than $1/\tau$, the membrane potential cannot catch up with the changes in the applied field, and the response of the membrane potential will be less than 100%. In general, the maximum membrane potential induced by a RF field is $$V(\omega) = 1.5 \, rE \cos \theta X(\omega) \quad (5)$$

where r, E and $\theta$ have the same meaning as in Eq. (1), $\omega$ is the angular frequency, and $X(\omega)$ is a function of the frequency such that $$X(\omega) = [1 + (\omega\tau)^2]^{-\frac{1}{2}} \quad (6)$$

when $\omega < 1/\tau$, $X(\omega)$ is near unity.
When $\omega > 1/\tau$, $X(\omega)$ decreases very rapidly with increasing frequency.

This frequency dependent effect can be used to fuse cells of different sizes. From Eq. (4), $\tau$ of the cell is roughly proportional to r. Thus the larger cell will have a longer $\tau$. To fuse the A and B cells, a pulsed RF electric field that has a frequency $\omega$ is applied such that $$1/\tau_a \angle \omega \angle 1/\tau_b \quad (7)$$

Since the frequency is less than $1/\tau_b$, $X(\omega)$ approaches unity for cell B and thus the field will produce a full effect on the small cell. On the other hand, since the frequency is greater than $1/\tau_a$, the induced membrane potential in cell A cannot fully follow the variation of the applied field, that is, $X(\omega)$ in cell A is less than unity. Thus, in a pulsed radiofrequency field, the effect of the stimulating field sensed by the small cell is greater than the effect on the large cell. Consequently, a pulsed radiofrequency field can be applied which induces a reversible breakdown of the membrane of the small cell without irreversibly damaging the larger cell.

One embodiment of a device 10 for poration and/or fusion of biological particles is shown in FIG. 1. It is a fusion chamber which includes a non-conducting container 13 for holding the solution 16 of biological particles 19. The container has a slightly concave bottom 22 so that biological particles 19 will congregate, under gravity, between the electrodes 25. The electrodes 25 are a pair of equidistant metal wires or metal bands made of nontoxic material, such as platinum or surgical stainless steel. The electrodes can be parallel wires or can be in almost any shape or design. The container 13 has an access port 28 wherein biological particles 19 can be added or removed.

Figure 2B:
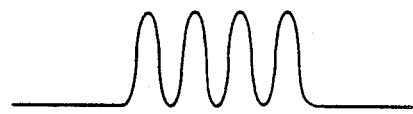
Figure 2C:
Figure 2D:
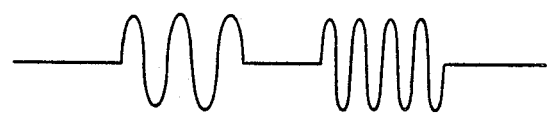
Figure 2E:
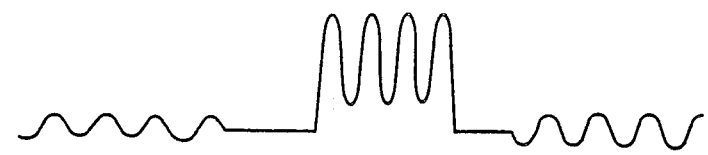
Figure 12C:
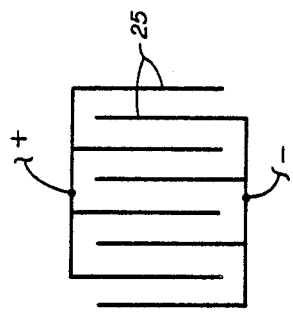
FIG. 12 is a schematic view of different designs for a bottom-contact electrode assembly. 12A is a top view of a square spiral assembly, 12B is a top view of a concentric square assembly, 12C is a top view of an interdigitating array assembly and 12D is a top view of a parallel plate assembly.
Figure 12B:
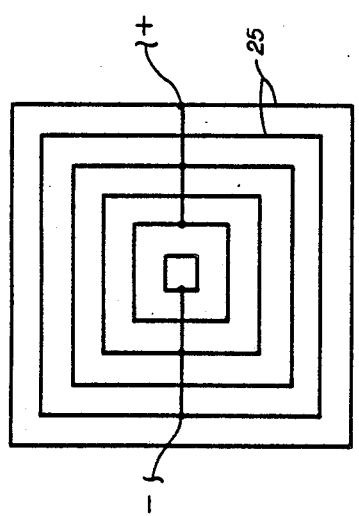
Figure 12A:
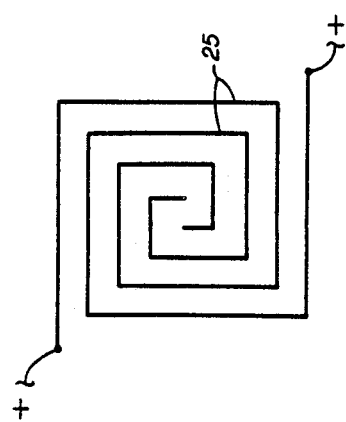
Figure 12D:
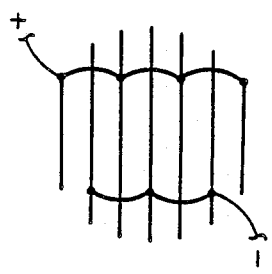

To induce cell-poration or cell-fusion, a high power function generator 31 generates one or many high power RF pulses which are applied through the pair of electrodes 25. The pulse shape can include one of those shown in FIG. 2. In FIG. 2A, the pulse is a symmetrical RF oscillation with a single frequency. In FIG. 2B, the RF pulse consists of a single frequency asymmetrical sinusoidal wave. In FIG. 2C, the RF pulse contains a mixture of sinusoidal waves of multiple frequencies (in this example, two frequencies). In FIG. 2D, alternating sinusoidal pulses of different frequency are used. In the preferred embodiment, the pulse shown in FIG. 2B is used, because it allows the applied energy of the field to be used more efficiently in inducing cell poration or fusion. Although the preferred RF electric field wave form is sinusoidal, other wave forms with repetitive shapes can be used. For example, triangular waves, square waves and sawtooth waves can be used to fuse or porate cells of different types.

One skilled in the art will readily recognize that the parameters of the pulsed field are changed to accommodate the characteristics of the different biological samples. The radiofrequency within the pulse may vary over the complete radiofrequency range of 10 KHz to 100 MHz. Typically a value in the order of 0.02 to 10 MHz is used for the poration and/or fusion of biological cells.

The width of the pulse may vary from about 1 μsec to 10 msec. In the preferred embodiment approximately 20 μsec to 2 msec is used.

The field strength is controlled by varying the pulse amplitude. For fusion and poration of cells the range of 1 to 20 kV/cm is employed. In the preferred embodiment pulses of field strength up to about 10 KV/cm are used.

The pulse can be a single pulse, a train of P pulses or multiple trains of pulses. A train of pulses are multiple pulses with an interval in between; for example, a series of ten pulses 0.5 milliseconds in width each pulse sePa- rated by 0.5 seconds. In some instances such as the fusion of HL-60 cells, the maximum fusion yield is enhanced by applying multiple pulses.

The RF pulses used for cell-poration and cell-fusion are similar. The main difference is that in cell fusion, the cells need to congregate (be brought into close proximity) before the high power RF pulse is applied. Furthermore, the cells must be maintained in close proximity after application of the RF pulse. The above described device brought the cells together by gravitational congregation. An alternative, and more efficient method of cell aggregation is dielectrophoresis, where a continuous alternating current (AC) electric field is applied across the electrodes before and/or after the application of the high-power RF pulse. The amplitude of this continuous AC field is typically in the range of 100 to 400 V/cm. Its frequency may vary from about 60 Hz to about 10 MHz. During cell fusion in the preferred embodiment the actual electric field applied across the electrodes may look like that shown in FIG. 2E. ;

Another device for poration and/or fusion of larger volumes of cells is shown in FIG. 3. An array of equidistant electrodes 25 instead of a single pair of electrodes is used to apply the AC field and the pulsed RF field. The bottom of this fusion chamber can be either flat or slightly concave. It is made of transparent material such as glass or clear plastic. This chamber can be placed on top of an inverted optical microscope so that the events of cell fusion and/or cell poration can be directly monitored. Since the effects of different experimental conditions can be assayed in a timely manner with the design, it will be useful for establishing the optimal condition for cell fusion and/or cell poration.

The electrodes can be arranged in any pattern, as long as they are maintained equidistant from each other. In the preferred embodiments the patterns have included interdigitating array, concentric circles and double spirals.

Another preferred device 10 for cell poration and cell fusion is shown in FIG. 4. This device 10 is designed to allow observation of cell fusion under an optical microscope using a small volume of cell suspension. This device is formed by two glass plates 34 separated by spacers 37 of approximately 0.3 mm thickness, with the cell suspension 19 sandwiched between the glass plates 34. In one embodiment thin glass plates such as cover slips are used. Electrodes 25 are two parallel platinum wires which are about 0.5 mm apart. The platinum wire electrodes 25 are connected to a high-power function generator 31. The high-power function generator can generate both alternating current electric fields and pulsed radiofrequency fields. An inlet tubing 41 and an outlet tubing 44 are used to insert and remove cells from the space between the electrodes.

Another embodiment of the present invention for cell poration and cell fusion is shown in FIG. 5. The purpose of this device is to porate or fuse a very large volume of suspended biological particles; including biological cells, protoplasts, bacteria and yeasts. This device 20 is designed for ease in application, maintenance, and cleaning. The cell suspension is contained in a non-conducting cylindrical container 13. The electrode assembly 50 is attached to an insulating handle 47. To porate or fuse the suspended cells, the electrode assembly is lowered into the cell container 13 by manipulating the handle 47. The electrodes 25 are connected to the high-power function generator 31 by a connection means 49. The AC field for cell fusion and the high Power RF pulses for cell Poration and/or cell fusion are then applied through the electrodes 25 in the electrode assembly 50.

In this device 20 the electrode assembly 50 is a vertical cylinder 53 and metal electrodes 25 are exposed at the side (i.e., the cylindrical surface). The cylinder can be any non-conducting material, for example, glass, plastic, or teflon. When the electrode assembly 50 is lowered into the cell container 13, the suspended cells 19 are displaced and form a thin layer of cell suspension 19 surrounding the electrode assembly 50. Thus, all cells are in close proximity of the electrodes. When an electrical potential is applied across the electrodes, the cells are exposed to the electric field.

One design of the electrode assembly 50 is shown in FIG. 6. Two metal wires or bands are coiled to form a double helix electrode 25. The helices are identical in shape except one is positioned between the other. These two helices are attached to a cylindrical support 53. The spacing between these two helices 25 is kept constant. Thus, when an electrical potential is applied across the two metal wires, the amplitude of the electric field generated between the two helices is uniform along their entire length.

Another embodiment of the electrode assembly 50 for cell poration and cell fusion is shown in FIG. 7. Here the electrode 50 assembly is comprised of a stack of metal ring electrodes 25 separated by non-conducting insulating spacers 53 of fixed thickness. These ring electrodes 25 are connected together in an alternating fashion to form two sets of electrodes 25, each of which is then connected to the output terminals of the high-power function generator. The rings have an attachment means 56 and a hollow area 59 for the passage of the wire to the alternate electrode 25.

The electrodes 25 do not have to be circular, but can be any shape. Shapes which can be used include circular, rectangular as in FIG. 8 or eliptical.

Another embodiment for cell poration and cell fusion is shown in FIG. 9. The cell suspension 19 is contained in a non-conductive container 13. An electrode assembly 50 is attached to a handle 47 which can be used to manipulate the position of the electrodes. Unlike the previous devices, the electrodes of this embodiment are exposed at the bottom of the electrode assembly 50. This device is thus particularly useful in porating and/or fusing cultured cells that attach to the bottom of culture dishes.

One design of the bottom-contact electrode assembly 50 is shown in FIG. 10. The electrode assembly 50 consists of two spirals of metal bands, which serve as the "ground" (−) and "high voltage" (+) electrodes 25. The two spirals are positioned in such a way that the spacing between each spiral is maintained constant. The equal spacing arrangement ensures that an applied electric field across the two electrodes 25 is uniform in strength throughout the entire area covered by the electrode assembly.

In addition to the spiral design, other configurations including, multiple concentric rings, rectangular shapes, interdigitating arrays, parallel plates or eliptical shapes can be used (see FIGS. 11 and 12). The rings or shapes connected in alternating fashion into two groups. One group of these rings or shapes is connected to the "ground" (−) terminal, while the other group of rings or shapes are connected to the "high voltage" (+) terminal of the high-power function generator. The spacing between the rings or shapes is constant so that the strength of the electric field generated between the adjacent rings or shapes is uniform throughout the entire assembly. In the bottom-contact electrode assemblies, the electrodes can be wires, plates or bands. In the preferred embodiment, the width of the electrodes is greater than the depth of the cell suspension.

Figure 13C:
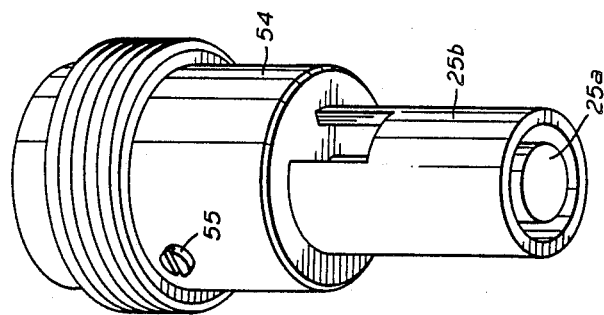
FIG. 13 is a schematic of a probe for cell poration and cell fusion of a small number of cells using the RF method. The exterior of the metal electrode is designed to fit inside the wells of a 96-well cell culture plate. 13A is a three-dimensional view of the probe, 13B is a cross-sectional view and 13C is a fragmentary elevational view of the electrode.
Figure 13B:
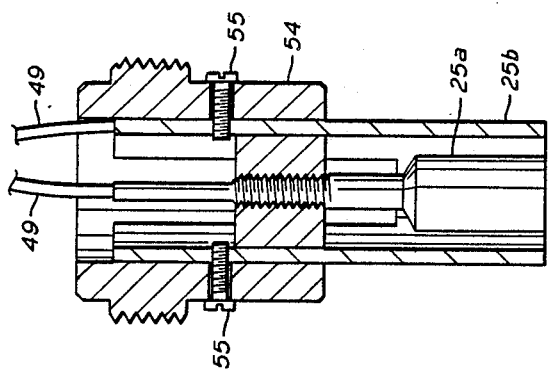
Figure 13A:
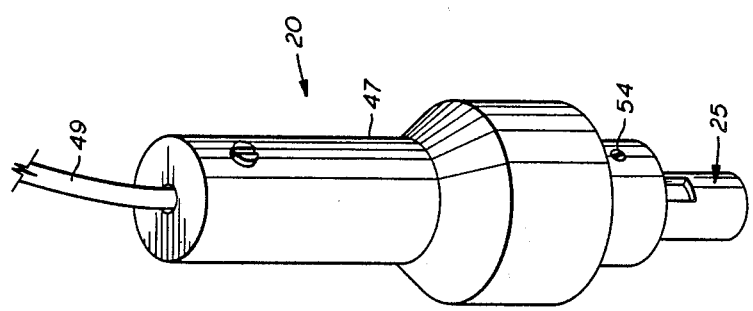

Another embodiment of the present invention for cell poration and cell fusion is shown in FIGS. 13A–C. The probe 20 allows cell fusion or gene transfection for a small volume of cell suspension. The probe 20 will fit into a flat-bottomed 96-well cell culture plate, for example Corning model 25860. The probe 20 includes two coaxial electrodes 25. The inner electrode 25a is a solid cylinder and the outer electrode 25b is a hollow tube. The coaxial electrodes 25 can be made of a variety of conductive materials. In the preferred embodiment, the coaxial electrodes 25 are made of stainless steel. The coaxial electrodes 25 are attached to a nonconductive insulating holder 54 preferably made of teflon or plastic.

The gap between the inner 25a and outer 25b coaxial electrodes may vary from about 0.5 to 2.0 mm. In a preferred embodiment, the electrode 25 has a 0.7 mm gap. With this probe 20 the total volume of suspended cells to be fused or porated is about 80 μl and it is possible to do cell fusion or cell poration with as little as 20 μl of cell suspension.

The probe 20 has a handle 47 made of non-conductive material, preferably teflon. Holding means 55, hold the outer electrode 25a in place.

This design has several advantages. Besides allowing the use of small volumes of cell suspension for cell fusion or cell poration, it is also simple to use and highly cost-effective. Unlike most commercial machines which require one cuvette to transfect one cell sample, this probe can serially transfect many cell samples using plates with multiple wells.

Figure 14:
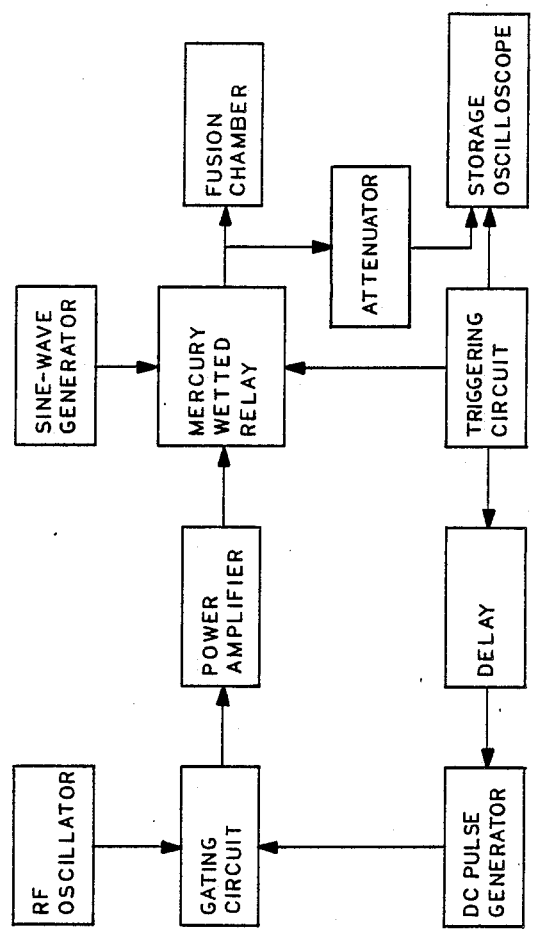
FIG. 14 is a block diagram of the apparatus which provides the source of the AC field for dielectrophoresis and the high-power RF pulses for cell poration and/or cell fusion.
Figure 15:
FIG. 15 is an electron micrograph showing the surface of a human red blood cell following RF poration treatment. Three RF electric field pulses were applied with a one second interval. The cells were rapidly frozen in liquid freon which was cooled by liquid nitrogen (Temperature 90° K). The frozen sample is examined by freeze-fracture electron microscopy. Magnification 50,000X.

Another embodiment of the present invention for cell poration and cell fusion is shown in FIG. 14. This figure shows the block diagram of the high power function generator which generates both the AC field for dielectrophoresis and the high power RF pulses for cell fusion and/or cell poration. The switching between the AC field and the RF field is controlled by a mercury wetted relay. The RF pulses are generated by gating the output of a radiofrequency oscillator and then passing through a MOSFET power amplifier, the power output of which may be as high as twenty kilowatts.

Alternatively the AC field and the pulsed RF field can be generated by synthesizing the required electrical wave with a digital computer and amplifying these wave forms using a power amplifier. In this embodiment the protocol can be controlled entirely by the computer and thus no switching relay is needed. This computer-synthesized high power function generator has several advantages. First, very complicated wave forms can be generated to optimize the fusion and/or poration of different types of cells. Second, when the high power function generator is used in more than one protocol or by more than one user, each protocol can be stored separately in a data storage device for example, a magnetic diskette. Since the protocols can be recalled quickly, the high power function generator can be reprogrammed to generate the desired wave forms without manually readjusting all the parameters. Third, the same computer can be used as a digital oscilloscope to record the actual electrical field apPlied to the cells. This record can be saved in a data storage device as the permanent record of any particular cell fusion or cell poration experiment.

Excessive current is harmful to the cell because of the resulting thermal effects and PH changes. To avoid generating excessive current and the resulting effects during the application of the electric field, the suspension medium of the cells is usuallY a low ionic strength solution. Preferably it contains very low concentration of salts. A typical suspension medium may contain 1 mM of electrolyte including 0.4 mM Mg-acetate and 0.1 mM Ca-acetate. The medium is buffered and the pH maintained in the physiological range, for example, pH 7.5. Any buffer commonly used for biological purposes, for example, 1 mM HEPES (N-2-hydroxyethyl-piperazine-N'-2-ethane sulfonic acid) is adequate for cell poration and/or cell fusion. Non-electrolytes are added to maintain the osmolarity of the medium at about the osmolarity of extracellular fluid. In the preferred embodiment, relatively high molecular weight, cell impermeable carbohydrates, such as sucrose and mannitol, are used to maintain the osmolarity.

For some cells, a slightly higher ionic strength in the medium seems to improve the fusion yield. For example, human erythrocytes fuse easily in 30mM Na-phosphate. Thus, the present method of fusion can use suspension medium with an ionic strength ranging from 0.1 mM to 100mM depending on the cell type.

The present invention for cell poration and cell fusion has a variety of uses. Many biological active substances, including DNA, RNA, organic chemicals, inorganic chemicals, drugs, antibodies, proteins, hormones, growth factors, enzymes and radio- or fluorescent-labelled molecular probes normally cannot be readily taken up by cells. The present invention provides an effective method to transport these biological active substances into the cells. In one embodiment of the present invention, cells can be temporarily permeabilized, that is porated, by applying high-power RF pulses and the biological active substances can then enter the cells during this poration period. The porated cells can be biological cells (including, animal, human or plant cells), protoplasts, bacteria or yeasts. In another embodiment of the present invention, the biological active substances can be inserted into the cells by fusing the target cells with other biological particles which have been pre-loaded with the active substances. Such biological particles include liposomes and erythrocyte ghosts, which can be easily preloaded with desired substances using a standard osmotic shock and dialysis method. (Schlegel & Lieber *Cell Fusion* ed by A.E. Sowers Plenum Press (1987)). The target cells may be any cells which will receive the biological active substances and include isolated cells, egg cells, embroyonic cells, any primary or transformed cultured cells, or other cells in vitro.

In like manner, biological substances could be extracted from biological cells. For example, many molecules such as hormones, growth factors, enzymes, proteins and nucleic acids may not be able to cross the membrane barrier. Using the poration method of the present invention, temporary pores can be induced in the cell membrane. The non-permeable molecules can then exit the cell. This procedure could be useful in a variety of industries which use growing cells to produce biological molecules. This procedure allows the extraction of these molecules without having to kill the cells.

EXAMPLE I

The ability and efficiency of the RF electroporation method to insert foreign genes into the target cell is examined using the cultured eukaryotic fibroblast cell line COS-M6 (M6). Chloramphenicol AcetylTransferase (CAT) DNA was used as a gene marker. Bacterial CAT DNA was inserted into a plasmid vector (pSV$_2$-CAT). The CAT enzyme is not endogenously produced in mammalian cells, such as M6. Thus, the amount of CAT gene incorporated into the target cells can be assayed by monitoring the amount of CAT enzyme produced after the transfection.

The protocol was to apply 3 trains of high-power RF Pulses at 10 sec intervals. Each train consists of 5 pulses (frequency 100 KHz, field strength 2.5 KV/cm, pulse width 0.5 msec).

The RF poration protocol of the present invention is a highly effective method of gene transfection. In the conventional methods of gene transfection, for example, the calcium phosphate method or the DEAE-dextran method, usually requires at least 5-10 $\mu$g of plasmid DNA for each transfection. In previous electroporation methods that used DC pulses, even larger amounts of DNA (typically 10-40 $\mu$g) were required. (Ansubel et al., Current Protocals in Molecular Biology, John Wiley & Sons, 1988). Using the RF poration method of this invention, we obtained a high level of CAT activity (76% acetylation per 25 $\mu$g of protein) when M6 cells were transfected using only 0.1 $\mu$g of CAT DNA. Furthermore, up to 10.6% acetylation per 25 $\mu$g of protein was observed when M6 cells were transfected with as little as 0.01μg of CAT DNA. Thus, it is evident that the RF poration method has a much higher efficiency of gene transfection. The improved efficiency not only results in great savings in labor and material that is required to produce DNA, but also will allow the transfection of cells which were previously difficult to transfect.

Another advantage of the RF poration method is that it requires far less cells for gene transfection. The conventional chemical methods and the DC electroporation method typically require 2 to 10 million cells to do one transfection. With the RF method, M6 cells have been transfected with the CAT gene in high efficiency using as few as 0.1 million cells. Further experiments indicated that even lower numbers of cells ($1 \times 10^4$) can be used. Currently, the minimum cell number is limited by the amount of total cell protein required to perform the CAT assay and not the ability to transfect cells. (Typically 25 micrograms of total cellular protein are needed for the CAT reaction.)

EXAMPLE II

Because of the unique abilities of the RF poration method to transfect cells in small quantity and with high efficiency, the method will be particularly useful in the development of gene therapy. Many diseases are known to be caused by genetic defects. Such diseases could be treated by inserting a therapeutic gene into human cells such as bone marrow stem cells and then transplanting these cells into the human body.

For example, patients with sickle cell anemia have a defective gene which produces abnormal hemoglobin. To treat such a genetic disease, bone marrow stem cells are extracted from the patient and transfected with the normal hemoglobin gene. The transfected stem cells are transplanted back into the patient. With the appropriate vector the normal gene will be stably integrated into the genome and the patient will be able to produce normal hemoglobin.

The key step in this treatment is the transfection of the bone marrow stem cells with the normal gene. Because the number of stem cells which are extracted is relatively small, a gene transfection method of high efficiency that is suitable for extremely low cell numbers is required. The method of the present invention of poration using RF pulses uniquely has this ability. Thus this method will be highly useful for gene therapy.

The usefulness of this method for gene therapy is not limited to sickle cell anemia. This method can be applied to insert normal genes into human cells to cure many genetic diseases. Other examples include: introducing the gene for clotting factor VIII into bone marrow stem cells to cure hemophiliacs; inserting the gene for insulin into pancreatic islet cells or other human cells to treat diabetes; introducing the gene for the human LDL (low density lipoprotein) receptor into liver cells or other human cells to lower the cholesterol level in the bloodstream of hypercholesterolemia patients; and introducing the gene for human growth hormone into human cells to correct growth defects. Thus, the possibilities of using this method to insert genes into human cells to treat genetic diseases is unlimited.

EXAMPLE III

Morphological Changes of the Cell Membrane during the Process of RF Field Electroporation A fraction of a second after human red blood cells were exposed to RF pulses, they were rapidly frozen in liquid freon cooled by liquid nitrogen. The structure of the cell membranes were examined using the technique of freeze-fracture electron microscopy. In FIG. 14 the electron micrograph shows the surface structure of the red blood cell after 3 RF pulses (400 kHz, 40 μsec wide, 5 kV/cm field strength) were applied. Membrane pores with diameters of 0.1 to 0.3 micrometers were clearly seen. These pores are sufficiently large to allow a large piece of DNA to easily diffuse from the extracellular medium into the cell. Thus, there is direct evidence that the applied RF fields can induce large pores at the cell surface. The morphological evidence clearly shows that the method of the present invention is effective in inducing membrane poration to allow transfection of cells with exogeneous genes.

EXAMPLE IV

Figure 16:
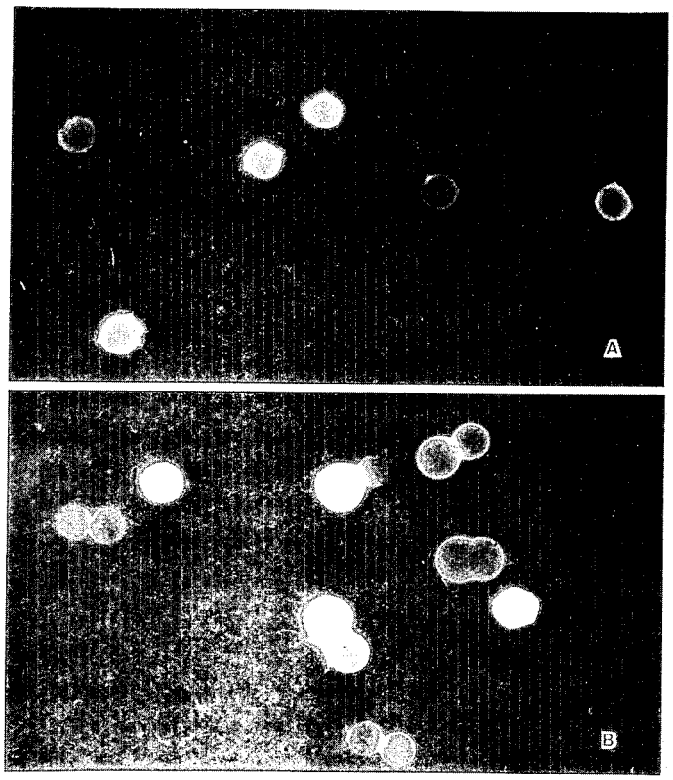
FIG. 16 is fluorescent micrographs showing the events of fusion between human red blood cells. Red cells were lined up in pearl chains by the process of dielectrophoresis. Roughly 10% of the cells were prelabelled with a fluorescent dye which produced bright images under a fluorescence microscope, The unlabelled cells could not be seen. 16A shows how the cells looked before applying the RF pulses. No transfer of dye between labelled and unlabelled cells was seen. 16B shows how the cells looked 4 minutes after 3 RF pulses (40 μsec wide, 300 KHz, 5 KV/cm were applied. Some of the labelled cells fused with their unlabelled neighboring cells, allowing the fluorescent dye to transfer between them.

An example of the advantage that the present invention has over the conventional DC (direct current) electrofusion method was seen in the fusion of human erythrocytes. The fusion events were assayed by labelling the membranes of a small number of the suspended cells with a lipophyllic fluorescent dye, for example, 1,1',-dihexadecyl-3,3,3'',3'-tetramethylendocarbacyanine perchlorate. The cells were observed with a fluorescence microscope. Before applying the RF pulses, only the prelabelled cells give a fluorescent image and they appeared as isolated cells (see FIG. 16A). After the cells were exposed to pulsed RF fields, unlabelled cells started to fuse with labelled cells and the dye was gradually transferred from the labelled cell to the unlabelled cell. Eventually both cells became labelled (see FIG. 16B). This fusion process took only a few minutes following the application of the RF pulses.

Figure 17:
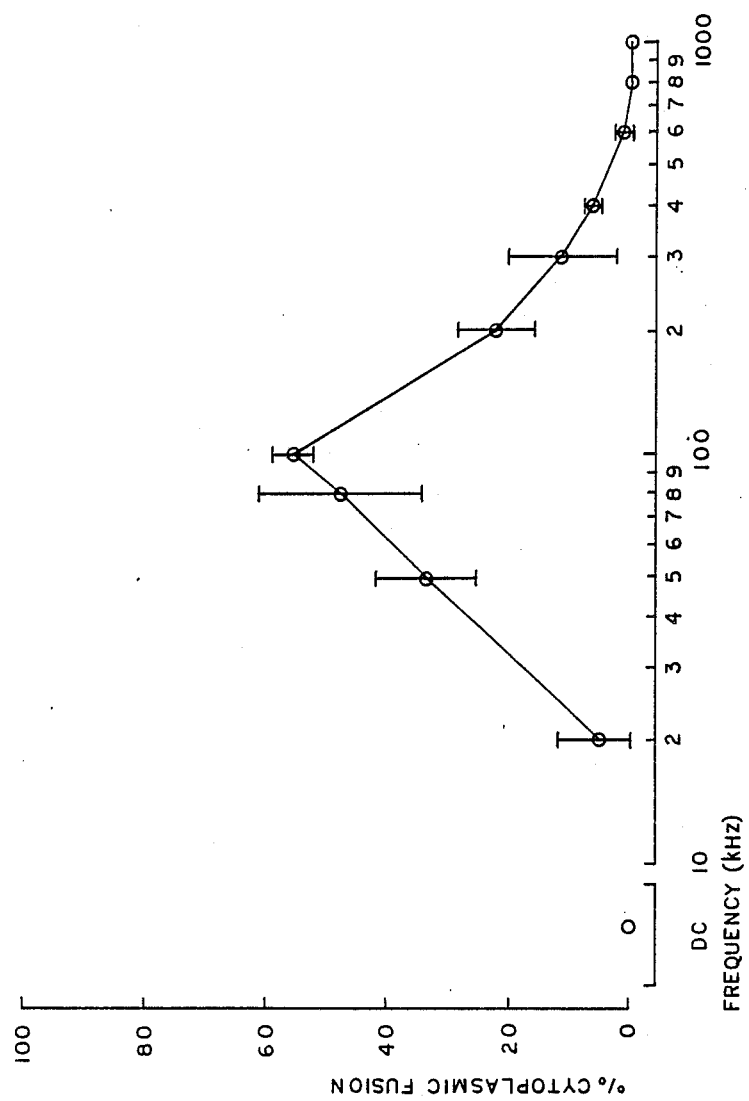
FIG. 17 is a graph showing the measured fusion yield between human red blood cells using three electrical pulses (4 KV/cm, 100 μsec). The fusion yield is shown to vary with the oscillating frequency.

Two types of cell fusion were observed in this experiment: (1) Membrane fusion, in which the fluorescent dye was transferred from the labelled cell to the unlabelled cell but the two cells did not merge their cytoplasm; and (2) cytoplasmic fusion, in which the fusing cells merged together to form one single large cell. The percentage of cells undergoing cytoplasmic fusion depends strongly on the oscillating frequency of the applied RF field. The fusion yield for erythrocytes after RF pulses of different frequency are applied is shown in FIG. 17. The highest yield of fused cells occurred when the applied RF field was oscillating at 100KHz. The fusion yield decreased to a very low level as the frequency became too high or too low. No cytoplasmic fusion was detected when the applied field was in the form of DC pulses with the same pulse amplitude and pulse width as the RF pulses. These results clearly indicate that the RF pulse method of this invention is much more effective in inducing cell fusion than the DC pulse method.

Another example of the advantage of the present invention over the DC electrofusion method is in the fusion of human erythrocytes with a human leukemia cultured cell line, HL-60. Fusion of these two cells types was not obtainable using the DC pulse method. The failure is probably due to the differences in cell size; erythrocytes are significantly smaller than HL-60 cells.

However, using the fluorescent dye assay and the pulsed RF field of the present invention, we were able to obtain the fusion of erythrocytes with HL-60 cells.

EXAMPLE V

Figure 18:
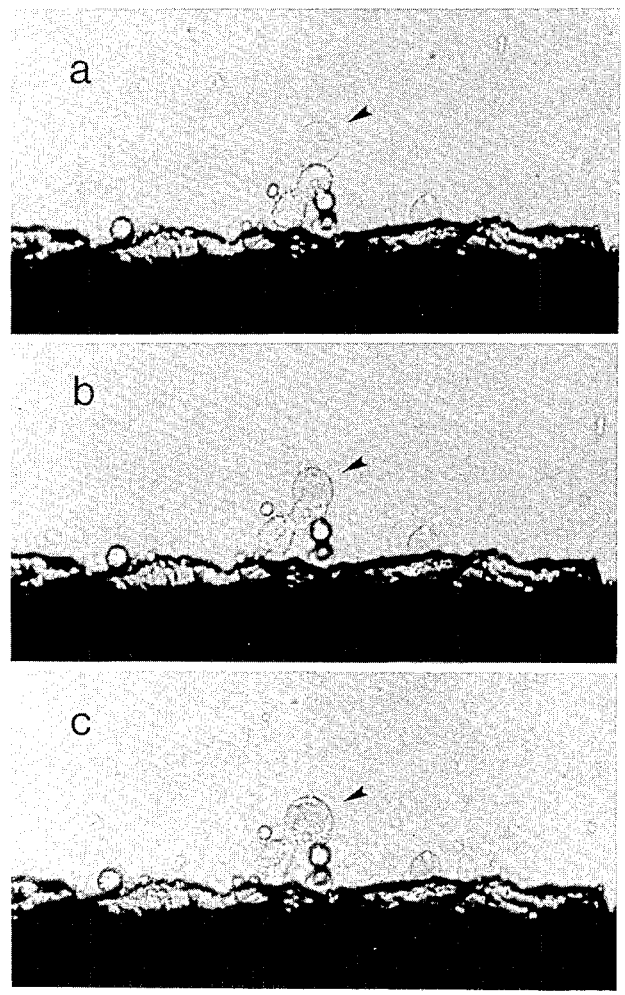
FIG. 18 is a time series of optical micrographs showing the fusion of a xanthophore cell with a fish tumor cell induced by pulsed RF fields. 15A is before fusion but after the xanthophore (marked by the arrow) was brought into close contact with two tumor cells by dielectrophoresis. 15B is two minutes after application of the RF pulses showing that the xanthophore has already begun fusing with one of the tumor cells. 15C is 4 minutes after application of the RF pulses showing that the xanthophore and tumor cell have completely merged into a single round cell.

The RF pulse method can be used to fuse cells to make hybridomas. Pigment cells from goldfish (xanthophores) were fused with a tumor cell line derived from fish skin cells. Because xanthophore cells have a built-in histochemical marker (the carotenoid droplets), it is comparatively easy to assay their fusion with non-pigmented tumor cells. FIG. 18 shows the sequential steps in the fusion of a xanthophore and a skin tumor cell. In FIG. 18A the cells were brought into close contact by dielectrophoresis. Three pulses of RF field (40 $\mu$sec wide, frequency 400 kHz, field strength 3.3 kV/cm) were then applied. Within two minutes the cytoplasms of the two cells begun to merge (see FIG. 18B). After 4 minutes, the cells completely coalesced into a single giant cell (see FIG. 18C).

An important application of forming hybridomas using the RF pulse method is to make antibodies, especially human monoclonal antibodies. In this instance the biological particles to be fused can include antibody producing cells (for example, lymphocyte B cells) and continuously dividing cells (for example, cancer cells). Using a selection process, the resultant hybridoma cells can be cultured to produce specific monoclonal antibodies.

One skilled in the art will readily appreciate the present invention is well adapted to carry out the objects and obtain the ends and advantages mentioned, as well as those inherent therein. The devices, methods, procedures and techniques described herein are presently representative of the preferred embodiments, are intended to be exemplary, and are not intended as limitations of the scope. Changes therein and other uses will occur to those skilled in the art which are encompassed within the spirit of the invention or defined by the scope of the appended claims.

What is claimed is:

1. A method of inserting foreign genes into biological particles comprising the steps of:
    placing a plurality of biological particles between electrodes in a solution contianing the foreign gene; and
    applying a pulsed radiofrequency oscillating electrical field across siad electrodes, wherein said pulsed radiofrequency includes a frequency range of less than 50 KHz and greater than 10 KHz or a frequency range of greater than 500 MHz to 10 MHz, a pulse width range of about 1 $\mu$sec to 10 msec. and a pulse amplitude of about 1 to 20 KV/cm.

2. The methof of claim 1, wherein,
    said biological particles are selected from the group consisting of human cells, animal cells, plant cells, protoplasts, bacteria and yeast.

3. A method of treating genetic diseases, comprising the steps of:
    inserting in vitro a gene into cells by placing a plurality of biological particles between electrodes in a solution containing the foregin gene;
    applying a pulsed radiofrequency oscillating electrical field across said electrodes; and
    transplanting said cells with the inserted gene into the organism with the genetic defect.

4. The method of claim 3, wherein the organism is a human.

5. the method of claim 3, wherein, the cells in which the gene is inserted are extracted from the organism with the genetic defect prior to the insertion steps.

6. The method of claim 3, wherein, the genetic disease is sickle cell anemia, the cells are bone marrow stem cells and the gene is the normal hemoglobin gene.

7. The method of claim 3, wherein, the genetic disease is selected from the group consisting of hemophilia, diabetes, hypercholesterolemia and growth disorders;
    the cells are selected from the group consisting of bone marrow stem cells, pancreatic islet cells, liver cells and other human cells; and
    the gene is selected from the group consisting of the normal clotting factor VIII gene, the normal insulin gene the normal low density lipoprotein receptor gene and the growth hormone gene.

8. The method of claim 3, wherein said cells are bone marrow stem cells.

9. The method of claim 3, wherein,
    said pulsed radiofrequency includes a frequency range of about 10 KHz to 10 MHz, a pulse width range of about 1 $\mu$sec to 1 msec. and a pulsed amplitude of about 1 to 20 KV/cm; and
    said biological particles are selected from the group consisting of human cells, animal cells, plant cells, protoplasts, bacteria and yeast.

* * * * *

UNITED STATES PATENT AND TRADEMARK OFFICE
CERTIFICATE OF CORRECTION

PATENT NO. : 4,970,154                                          Page 1 of 2
DATED      : November 13, 1990
INVENTOR(S): Donald C. Chang It is certified that error appears in the above-identified patent and that said Letters Patent is hereby corrected as shown below:

Column 5, line 9, before "RF" change "high-Power" to -- high-power --

Column 5, line 44, after "shows" add -- a --

Column 6, line 12, after "microscope" change "," to -- . --

Column 6, line 17, after "cm" add -- ) --

Column 6, line 38, after "the" change "descriPtion" to -- description --

Column 6, line 54, before "ghosts" change "erythroycte" to -- erythrocyte --

Column 6, line 65, after "and" change "0" to -- θ --

Column 7, line 4, change "whee" to -- where --

Column 7, line 6, after "microns" add -- ),--

Column 7, line 6, after "about" change "1000" to -- 1000 --

Column 9, line 6, move (4) to end of line

Column 9, line 19, change "1/π" to -- 1/τ --

Column 9, line 31, change "X(ω)=[1+(ωŷ²)]⁻¹" to -- $X(\omega)=[1+\omega T2]^{-1/2}$ --

Column 10, line 36, before "pulses" delete -- P --

Column 10, line 39, after "pulse" change "sePa-" to -- sepa --

UNITED STATES PATENT AND TRADEMARK OFFICE
CERTIFICATE OF CORRECTION

PATENT NO. : 4,970,154
DATED : November 13, 1990
INVENTOR(S) : Donald C. Chang

It is certified that error appears in the above-identified patent and that said Letters Patent is hereby corrected as shown below:

Column 10, line 59, after "2E." delete -- ; --

Column 13, line 37, change "apPlied" to -- applied --

Column 13, line 45, change "usuallY" to -- usually --

Column 17, line 48, change "siad" to -- said --

Column 18, line 6, change "methof" to -- method --

Column 18, line 21, change "the" to -- The --

Column 18, line 42, change "msec." to -- msec, --

Signed and Sealed this

Nineteenth Day of January, 1993

*Attest:*

DOUGLAS B. COMER

*Attesting Officer*         *Acting Commissioner of Patents and Trademarks*